(12) United States Patent
Molina trejo

(10) Patent No.: US 11,395,784 B2
(45) Date of Patent: Jul. 26, 2022

(54) SENSORIAL ELECTRONIC DEVICE FOR THE REHABILITATION OF PATIENTS WITH PARKINSON'S DISEASE

(71) Applicant: N-TECS LABS S.A. DE C.V., Mexico City (MX)

(72) Inventor: Rodrigo Molina trejo, Mexico City (MX)

(73) Assignee: N-TECS LABS S.A. DE C.V., Mexico City (MX)

(*) Notice: Subject to any disclaimer, the term of this patent is extended or adjusted under 35 U.S.C. 154(b) by 544 days.

(21) Appl. No.: 16/528,916

(22) Filed: Aug. 1, 2019

(65) Prior Publication Data

US 2020/0188210 A1 Jun. 18, 2020

(30) Foreign Application Priority Data

Dec. 18, 2018 (MX) .................. MX/U/2018/000781

(51) Int. Cl.
*A61H 23/02* (2006.01)
*A61M 21/00* (2006.01)
*A61H 1/00* (2006.01)

(52) U.S. Cl.
CPC .............. *A61H 1/00* (2013.01); *A61H 23/02* (2013.01); *A61M 21/00* (2013.01); *A61H 2201/0188* (2013.01); *A61H 2201/165* (2013.01); *A61H 2201/1638* (2013.01); *A61H 2201/5025* (2013.01); *A61H 2201/5092* (2013.01); *A61H 2201/5097* (2013.01); *A61M 2021/0022* (2013.01); *A61M 2205/3306* (2013.01); *A61M 2205/583* (2013.01); *A61M 2205/587* (2013.01)

(58) Field of Classification Search
CPC .......... A61H 1/00; A61H 11/00; A61H 23/02; A61H 23/00; A61M 21/00; A61M 2021/0022
See application file for complete search history.

(56) References Cited

U.S. PATENT DOCUMENTS

| 5,575,294 | A | * | 11/1996 | Perry | ................ | A45B 3/00 |
| | | | | | | 600/595 |
| 10,242,590 | B2 | * | 3/2019 | Yu | ................ | A61B 5/486 |
| 10,251,611 | B2 | * | 4/2019 | Marsh | ................ | A61B 5/742 |
| 2021/0186794 | A1 | * | 6/2021 | Seim | ................ | A61H 23/0254 |

FOREIGN PATENT DOCUMENTS

| BR | 202014025116 U2 | 12/2016 |
| MX | 3590 B | 12/2016 |

* cited by examiner

*Primary Examiner* — John P Lacyk
(74) *Attorney, Agent, or Firm* — Hoglund & Pamias, PSC; Roberto J. Rios

(57) ABSTRACT

This invention refers to a device that reduces and counteracts human motor symptoms (tremor in the upper limbs, muscular stiffness, bradykinesia or slowness in movements, postural disruptions, Parkinsonian walking and freezing in the walking) caused by Parkinson's disease. The device produces vibration by means of a micro-motor that can be modulated in time, speed and power. A laser diode generates a light that is projected in the ground in the form of a horizontal line, a Bluetooth module communicates this device with different intelligent electronic devices and with applications. These components are powered by a rechargeable handheld power source. The components are powered by a rechargeable handheld electric energy source.

20 Claims, 8 Drawing Sheets

SENSORIAL ELECTRONIC DEVICE FOR THE REHABILITATION OF PATIENTS WITH PARKINSON'S DISEASE

BACKGROUND OF THE INVENTION

Parkinson disease is a neurodegenerative disease that affects people who suffer in a different way. Some of the main motor symptoms are tremors, muscle stiffness, walking abnormalities, postural disruptions, and slowness of movement; such as an "OFF" state of the body or freezing conditions before, during and after walking.

As the disease progresses, symptoms of Parkinson's disease may begin to interfere with daily activities. Affected people may not be able to hold the cutlery firmly or they may find that the tremor makes it difficult to read the newspaper or ingest their food. People with Parkinson's disease often develop the so-called Parkinsonian walking that includes a tendency to lean forward, taking small quick steps, such as hasty, this postural instability, or deterioration of balance, makes the affected people fall easily causing serious injuries. Another symptom that they also experience is a reduction of movement in one or both arms because the muscles remain constantly tense and contracted, people who suffer from stiffness constantly feel pain when trying to move their limbs.

The "Freezing" is described by the patients as the feeling of having their feet stuck to the ground. Patients with this symptom may have problems initiating movement and can suddenly stop when they walk (they become "Frozen"). This condition causes a large number of falls.

The slowness in their movements is particularly frustrating because it can make the simple tasks become difficult. The person cannot quickly perform routine movements. The activities the patients used to do quickly and easily, such as grooming themselves or getting dressed, can take much longer.

According to the state of the art of the utility model No 3590, which mentions a device that generates modulated vibrations and decreases the symptom of the Freezing during the Parkinson's patients way of walking, our invention, aimed to be protected, claims the development of an improvement over the aforementioned device. The improvements made to the utility model No 3590 were able to decrease symptoms, such as tremor in the upper limbs, muscular stiffness, bradykinesia or slowness in movements, postural disruptions, Parkinsonian walking and freezing gait as well. The improvements made to such device will be explained below.

SUMMARY OF THE INVENTION

The device according to the invention produces vibration through a micro-motor that is powered by a handheld electric energy source (a battery), wherein the vibration produced may be modulated in time, speed and power.

Vibration helps Parkinson's patient to re-make walking and to make natural movements in case of suffering a Freezing episode, this device makes the body to work on a human-like reflects-basis, so that the vibration wakes up the body, taking the user out of a blocking state, caused by the so called Freezing.

The vibration generated by the micro motor in addition to reducing the Freezing helps to reduce and counteract the tremors in the hand that occur when the patient is resting or moving. Another benefit we obtain with the use of vibrations is the patient's posture improvement; thus, reducing patient's back and neck curving, improving and achieving the body balance increase, keeping a stable gravity center.

With the vibrations generated by the device, we managed to reduce the muscular stiffness caused by Parkinson's disease, obtaining an increase in the ranges of movement. Movements slowness or bradykinesia are reduced considerably with the use of vibrations; we managed that patients move with a considerable motor speed increase in their bodies. Likewise, with the use of vibrations, the Parkinsonian walking was reduced, the patients improved their strides and bracing when walking, as well as reducing the percentage of falls caused by this symptom.

To complete such device operation and to better obtain results, we placed a laser guide which is powered by a handheld energy source (battery), which creates a light that is projected linearly on the ground, this guide is known as the visual guide. The light projected on the floor serves to generate a sensory stimulus that helps to remove the patients from the blockade caused by the Freezing diminishing a large percentage of injuries caused by falls.

The patient should place the device on the body so that the vibrating motor is in contact with her/his skin, this in order for the user to feel the vibrations that have been programmed by the Physician, this depends on the treatment and the scope wanted to be obtained.

The laser light should always point to the floor to make the light projecting properly and producing the line effect we require. We have put a Bluetooth module in order to maintain communication between our device and an intelligent device (smartphone, computer, tablet or smart band).

Details and characteristic of this device are clearly shown in the following description and in the accompanying drawings.

DETAILED DESCRIPTION OF THE INVENTION

Figure 1:
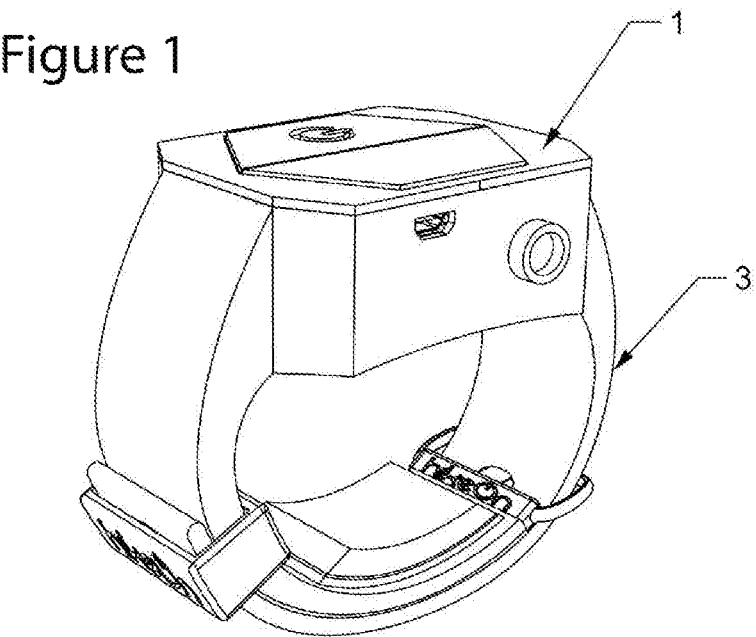
FIG. 1 is a plan view of the device assembled in its entirety that shows the left and the front side.
Figure 2:
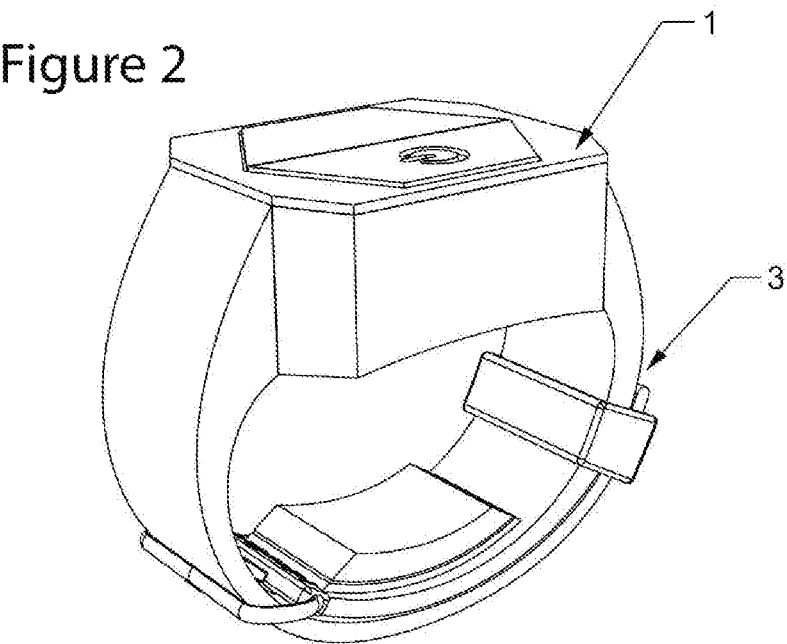
FIG. 2 is a perspective view of the fully assembled device that shows the right and back side.

The sensory electronic device for the rehabilitation of patients with Parkinson's disease referred to in the following invention (FIGS. 1 and 2) generates constant intermittent vibrating impulses using a vibratory motor that can be modulated in speed, intensity, time and frequency. The device also has a visual guide that is emitted by a laser diode module that is activated by a gyroscope that detects the inclination of the device, when the inclination is between 0 and 45 degrees (taking as reference that the floor is 0 degrees and 45 degrees are following the natural movement of the arm upward) the laser will project on the ground a light in the form of a horizontal line. This system as a whole, is focused on treating and reducing motor symptoms caused by Parkinson's disease (tremor in the upper limbs, muscular stiffness, bradykinesia or slowness in movements, postural disruptions, Parkinsonian walking and freezing during walking). The vibration and the visual guide serve to generate a muscular reaction in the patient, this creates a neuronal response resulting in the user improving and decreasing the symptoms mentioned above.

Figure 3:
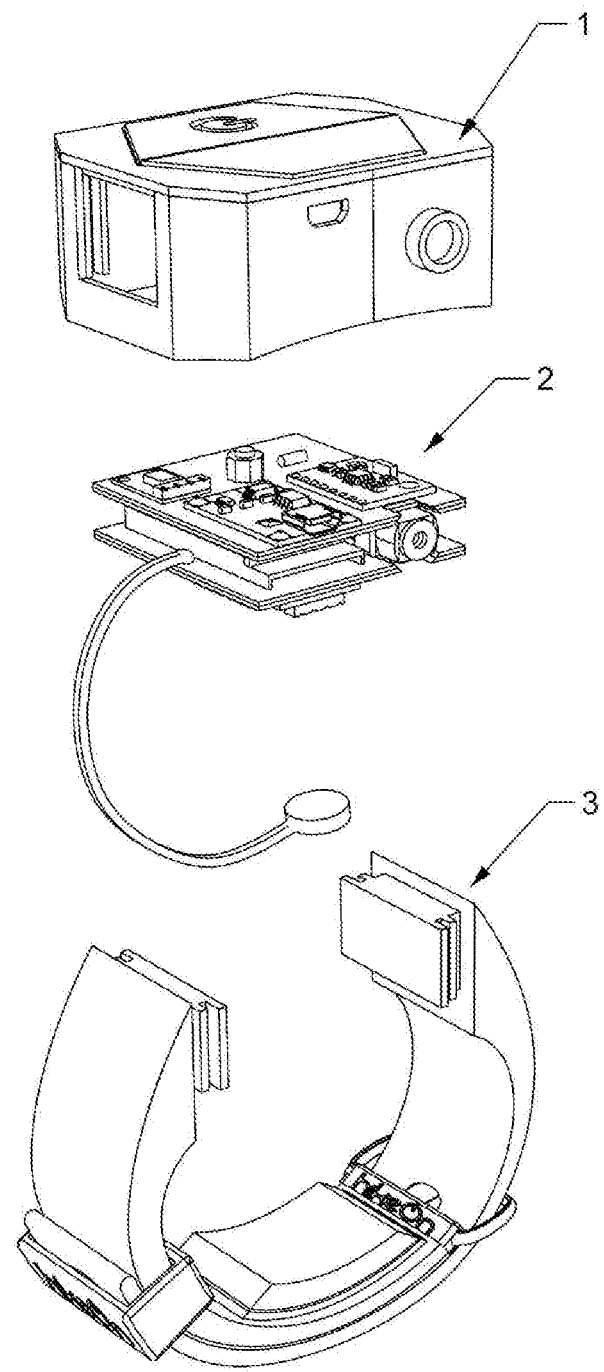
FIG. 3 is an exploded view of the device showing the left and front side, this view shows the three most important sets of the device.
Figure 4:
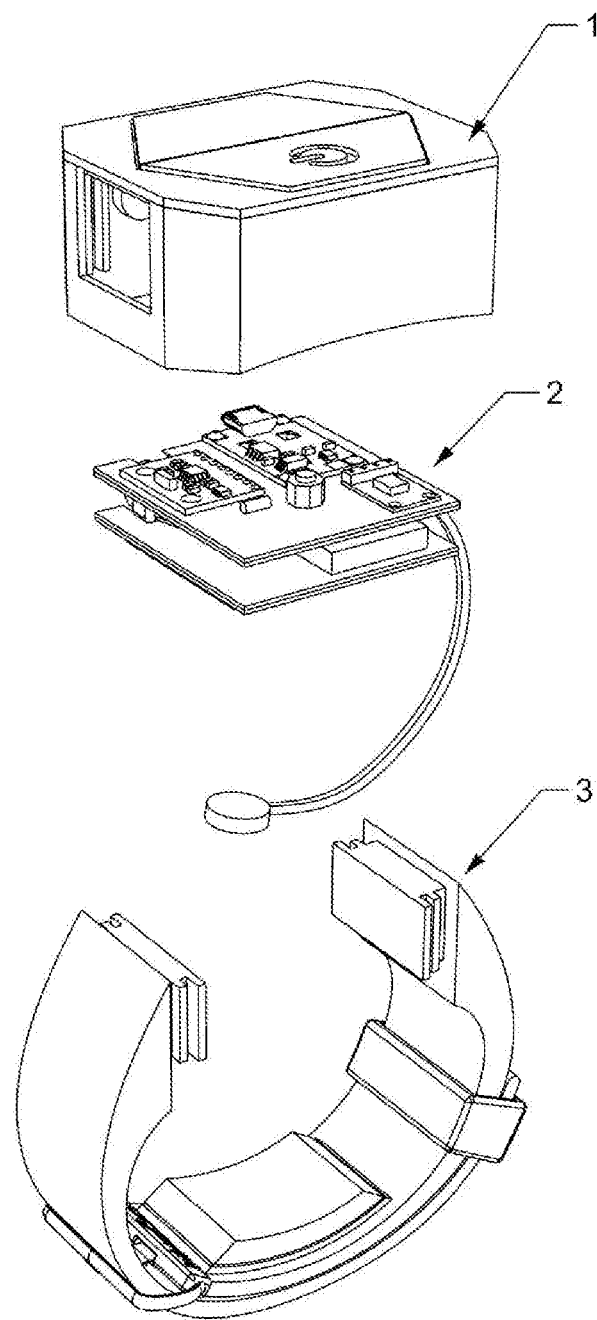
FIG. 4 is an exploded view of the vibrating device showing the right and back side, this view shows the three most important sets of the device.

The device is comprised by three groups (FIGS. 3 and 4), a casing (1), an electronic system (2) and a fastening system (3). These figures show an exploded assembly of the casing (1) made of rigid plastic that functions to cover and protect the electronics from any physical anomaly that could cause any damage. The electronic system (2) is in charge of the operation of the device converting the energy into modulated vibrations and in a light that will be projected as a linear guide in the ground. The fastening system (3) is in charge of securing the device and keeping it in contact with the patient's body.

Figure 5:
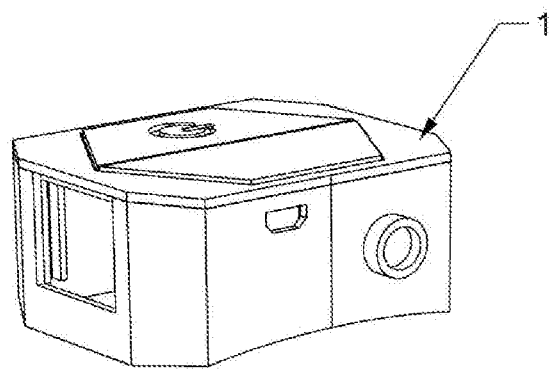
FIG. 5 is a perspective view of the casing showing the left and front side.
Figure 6:
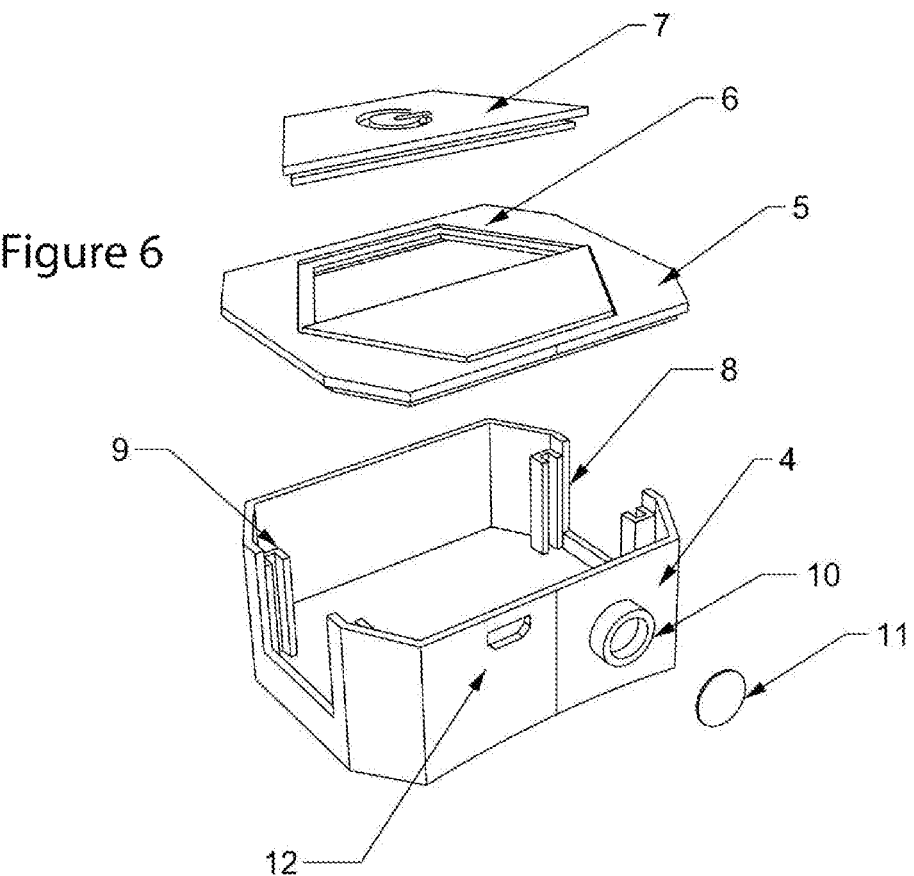
FIG. 6 is an exploded view of the device casing showing the components thereof, viewed from the left and front side.

FIG. 5 shows the casing which functions to cover and protect the electronic system from any external agent that could cause an anomaly and modify the operation inadequately. FIG. 6 shows the assembly of casing (1) where everything is mounted on the base of the housing (4) and a cover (5) is placed on top enclosing the entire electronics, this cover has a space (6) where one ON/OFF switch (7) is attached. The base of the housing has two rails on each of the sides (8) and (9) with a stop that is used to assemble the fastening system (3) assembly. The housing has a cylindrical-shaped protruding piece (10) which houses a special lens (11) which is responsible for transforming the light emitted by an infrared laser diode (13) into a visible horizontal line. An entry groove (12) is provided as an input to a battery charger cable.

Figure 7:
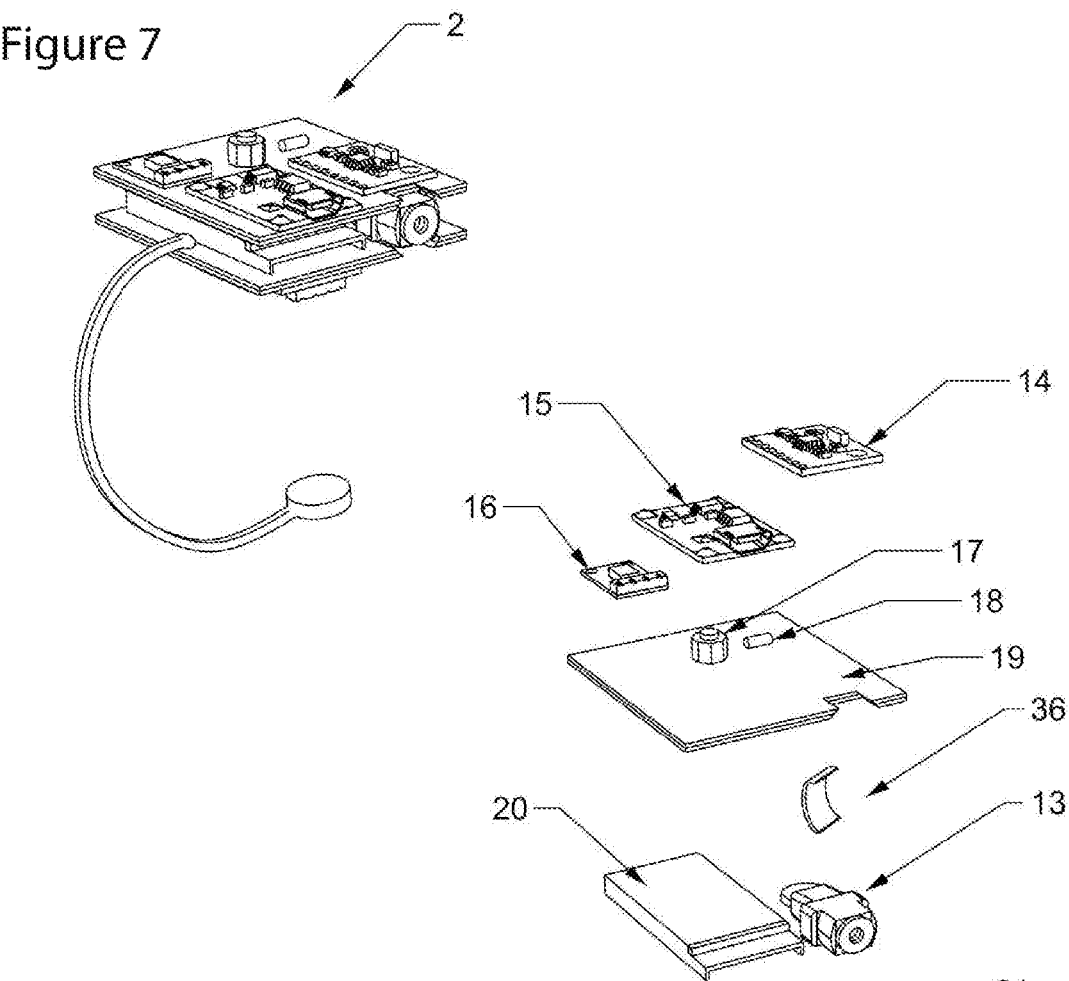
FIG. 7 is a perspective view of the device fastening system showing the left and front side.
Figure 8:
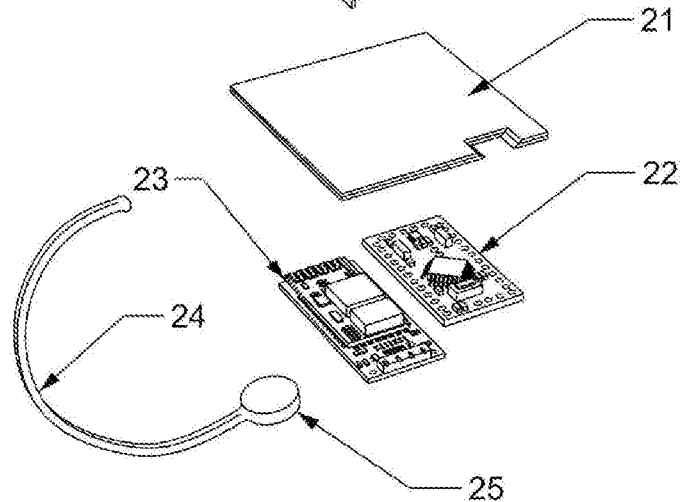
FIG. 8 is a perspective view of the device fastening system showing the right and back side.

FIGS. 7 and 8 show the electronic system. The device can be activated in two ways, mechanically and wirelessly through a Bluetooth connection protocol.

The device is mechanically powered up through a pulse switch known as the Start button (17). This button is one-way only button, (i.e., two-pin), one of its pins is connected to a positive pole trace of the circuit which comes from the main power unit provided by the lithium battery (20) and on the other side it is connected to a resistor (18) of 1 kohm which in turn is connected to a negative pole trace of the circuit which comes from the main power supplied by the Lithium ion battery (20), between the pin of the Start button (17) and the resistor (18) comes a line in the direct circuit to a wire of an 8-threads connector (36), this connector (36) communicates to the top plate (19) and the bottom plate (21), this wire of the Start button (17) signal leads to a digital input of the Arduino Pro Mini Microcontroller (22) to be read.

When pressing the Start button (17), a small or short tension drop is produced in the lithium-ion battery (20) which is protected from short circuit by means of the charging module for lithium-ion batteries (15) which also has the function of controlling the Battery power (15) when an external voltage source is connected. This small tension drop is sent by a line of the direct circuit to the micro Arduino Pro Mini Controller (22) in one of its digital inputs or outputs. When the Arduino Pro Mini Microcontroller (22) receives this signal, translates it into its programming as a power up action or command by means of a digital interlock or retention, this action causes that the Arduino Pro Mini Microcontroller (22), which is also connected to power lines in the circuit provided by the battery (15), produce an output voltage in two of the digital outputs of the same which is connected to the positive pole of the vibrating motor (25) and the negative pole of the same vibrating motor (25) is connected to Ground (its acronym GND), on the same circuit of the bottom plate (21) connected to the battery (15).

The other digital output is connected to the positive pole of the laser diode (13) and the negative pole to a GND on the bottom plate (21) connected to the battery (15). The vibrating motor (25) will convert these voltage pulses sent by the battery (15) and the Microcontroller (22), in mechanical vibrations and operate in intermittent mode, (i.e., high and low states), will vibrate for a short time and will be off by another, and these actions are given by milliseconds set in the programming of the Arduino Pro Mini Microcontroller (22). The laser is controlled by data sent by the gyroscope (14) to the Microcontroller (22). This gyroscope (14) communicates directly to the Microcontroller (22) by circuit means (traces), to analog inputs of the Microcontroller (22) and is powered directly from traces in the positive pole circuit and negative pole of the battery (15). If the data of the gyroscope (14) is equal to a sample programmed in the Microcontroller (22), it will take it as a 45 degrees inclination and will instruct to turn on the laser (13) through a digital output of the same Microcontroller (22) which will be in the form of positive voltage provided by the battery (20). If the data sent from the gyroscope (14) to the Microcontroller (22) do not coincide with the programmed sample, then the Laser diode (13) will remain off. To stop this action or to stop the vibrating motor sequence (25) and the laser (13), it is necessary to press the start button (17) again to send a signal once again, in the form of voltage drop produced by the battery (15) to the Arduino Pro Micro Mini Controller (22) through a trace of the circuit via a connector wire (36). This in turn will receive it, and due to the programming given, compares the status of the start button (17) digitally, (i.e., it confirms whether it was locked or not in the internal programming) and if so, it will break this sequence automatically by removing the digital interlocking and stops sending positive voltage by the digital signals connected to the positive poles of the vibrating motor (25) and the gyroscope (14) which is the one that makes the laser work (13). All these actions to read the status of the start button (17) are performed in a period of 100 milliseconds. After the action has been completed, the electronic component device or assembly will remain in the standby state only powered by the battery power (15) without any action until the start button (17) is turned on again or activated digitally.

In the digital form, the modules like gyroscope (14), RGB led (red, green, blue) (16), laser diode (13) and Bluetooth (23) remain always in a resting state powered from a battery (15) connected to traces in the positive pole circuit and negative pole on the top plate (19) and bottom plate (21) communicated to each other by a connector (36), its battery consumption (15) is minimal as long as the order of data reading or transmitting is given by an application specially designed to work with this device. For the general operation of the device it is necessary to have a smartphone with Bluetooth connection and with the application installed for this device. The first step is to link the smartphone with the bracelet, this is done through the "Link Bluetooth devices" section on the phone. The Bluetooth device (23) is connected to the Arduino Pro Mini (22) on the bottom plate (21) and sends only one detection signal in a standby state, linking the device. Once linked it returns to the application on the smartphone for the device and opens. When it opens, a menu with different tabs or function options for the device will appear. One option is to activate the laser guide light which is emitted by the laser diode (13) connected on the lower plate (21), by pressing the "guide" tab, the application will send a command through the communication protocol of the Bluetooth Module (23), this in turn is connected to the Arduino Pro Mini Microcontroller (22) through the traces designed on the direct circuit bottom plate (21) to analog inputs of the Arduino Pro Mini Microcontroller (22) and powered from one of the positive and negative pole traces direct from the Battery (15). The Microcontroller (22) will decode this command received by the Bluetooth module (23) and will activate the Gyroscope module (14) which is also connected to the Arduino Pro Mini Microcontroller (22) by one of its analogue inputs designed in the upper circuit plate (19) and through a connector (36) between the top plate (19) and the bottom plate (21) and is powered from one of the battery (25) positive pole and negative pole on the top plate. When sending this activation signal, the Arduino Pro Mini Microcontroller (22) wakes up or performs the gyroscope reading (14), this in turn sends positioning data on the X, Y, Z axes. The Microcontroller (22) receives this data and through its established programming, evaluates the data and makes a match. Its programming is designed so that when the gyroscope sends data equal to a sample already established to calculate 45° of inclination then the Microcontroller (22) will send a signal of positive voltage through one of its digital outputs to activate the laser diode (13) taken from the battery power (15), the gyroscope (14) will continue to send data and the Microcontroller (22) will continue to match the sample until the data does not coincide and it stops sending positive voltage through that digital output, taken from the battery (15). This action represents when the user's arm lowers the laser (13) and when he/she raises his/her arm it will be turned off. This action can be cancelled by selecting the "guide" tab again in the smartphone application, receiving the Microcontroller (22) the same command through the Bluetooth module (23) wherein the current state of the gyroscope (14) will be matched again and if it is active, it will deactivate it and send it back to standby status, leaving the readings to this module.

Another tab is the "color" tab that regulates the RGB Led (red, green, blue) (16) connected to the top plate (19) and is powered by one of the positive and negative pole traces of the battery (15). In this tab there is a color selector with boxes indicating the colors available. When a box of the color of preference is selected, the application sends a command through the Bluetooth protocol to the Bluetooth module (23) which in turn is connected to the Microcontroller (22) through the traces of the direct circuit to the analog inputs of the Microcontroller (22). The Microcontroller (22) decodes this command and through three of its digital modulation outputs by width or pulse, (PWM pulse width modulation, in English) will vary the intensity of positive voltage of each digital output taken from battery (15) to each LED RGB pin (16). By varying the intensity on the pins, the battery voltage (15) through the Microcontroller (22) is transformed into a different color light.

This action can be canceled by selecting again the "colors" tab and the application sends the signal by the Protocol of the Bluetooth Module (23) to the Microcontroller (22) and this in turn will stop sending positive voltage by its digital PWM outputs taken from the battery (15).

Figure 9:
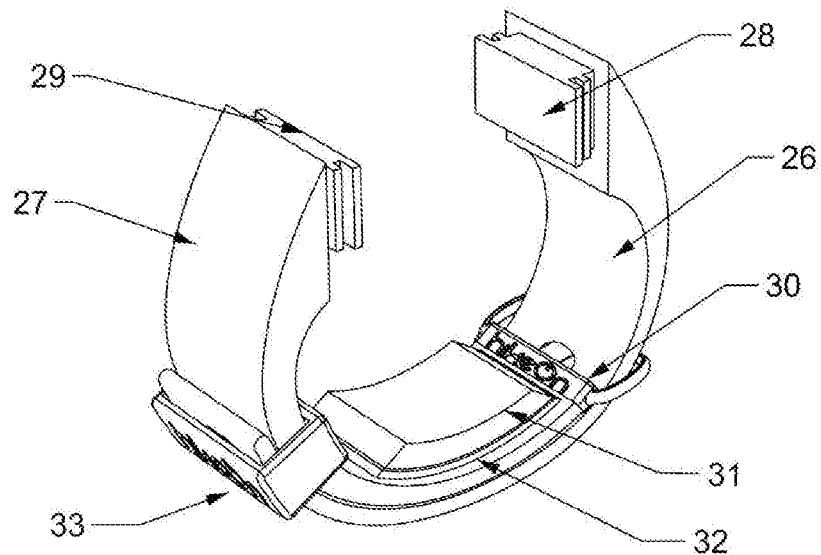
FIG. 9 is an exploded view of the device fastening system showing the right and back side.
Figure 10:
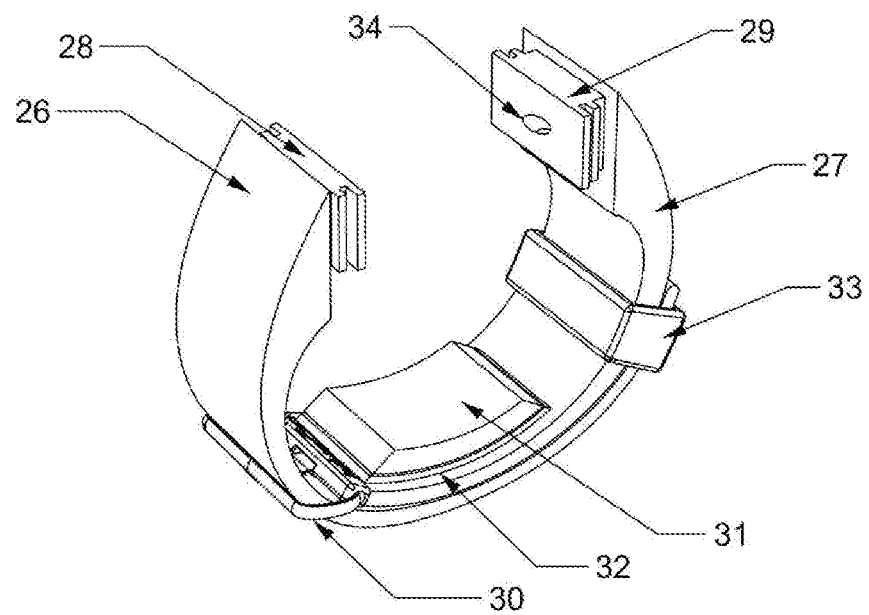
FIG. 10 is a perspective view of the electronic system that controls the entire device showing the left and front side.
Figure 11:
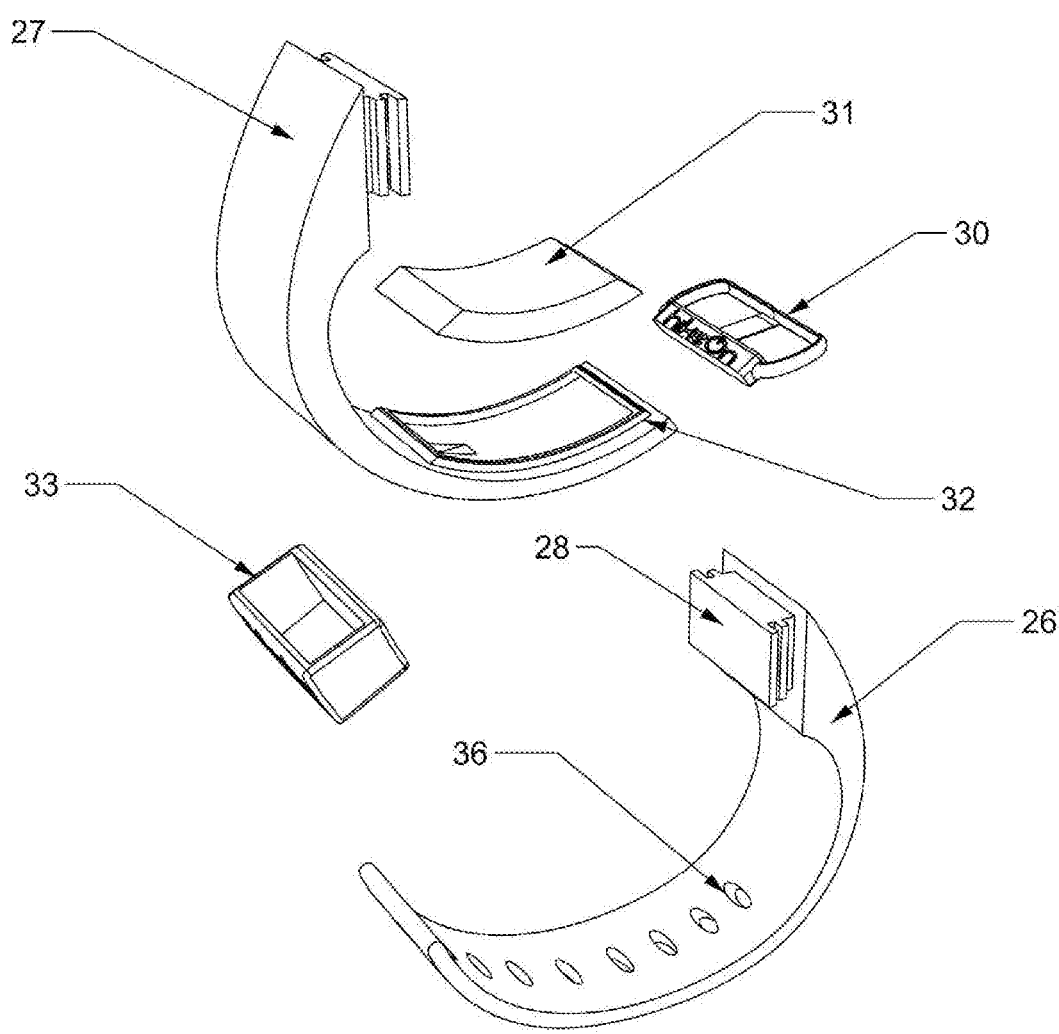
FIG. 11 is an exploded view of the device electronic system showing the left and front side part.
Figure 12:
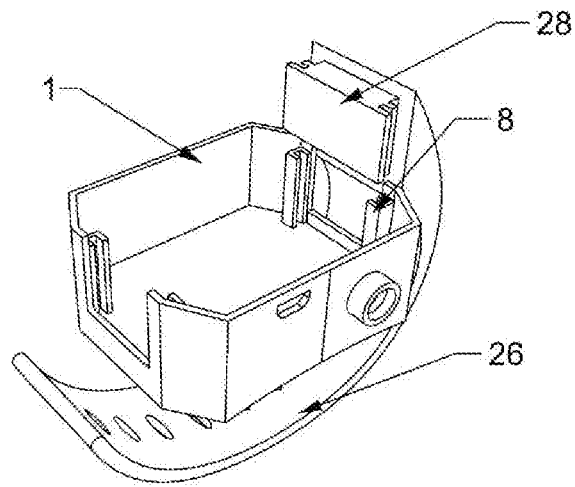
FIG. 12 is a perspective view of the assembly between the housing and the fastening system of the device showing the right and front side.
Figure 13:
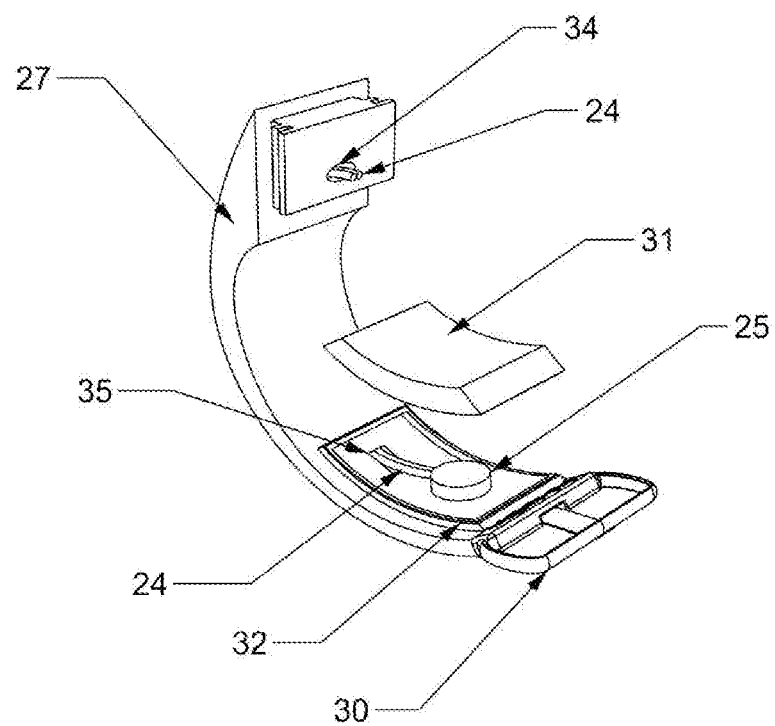
FIG. 13 is a perspective view of the vibration system assembly, and the device fastening system showing the right and front side.

The fastening system (3) is responsible for securing the device and keeping it attached to the limbs of the patient's body (FIGS. 9, 10 and 11). This group consists of two extendables (26 and 27), the first of these (26) has on the upper part a sliding assembly system (28) that attaches to the side of the housing base (8) to fit the system in order to join these two pieces (FIG. 12). The extendable (26) has holes (36) which are used to close the fastening system with the buckle (30). The extendable (27) has the same sliding assembly system (29) that is placed in the groove (9). This extendable (FIG. 13) has an inner hole that goes from the top (34) and ends at the bottom (35) in order to serve as a conduit for the wires (24) that connect the phenolic plate (21) to the motor that generates the vibration (25). The vibration motor guard system consists of a soft plastic cover (31) that is mounted on the base of the extendable (32) thus, preventing the motor from being exposed and being damaged by any external agent. A plastic strip retainer (33) on the extendable (27) holds and prevents the extendable movement (26). A V-Shaped extendable buckle (30) secures and joins both extendable and prevents any possible device falls.

The invention claimed is:

1. A sensory electronic device for the rehabilitation of patients with Parkinson's disease comprising:
    an electronic system including a control unit, a vibration motor, a gyroscope, a laser diode and a color LED;
    a casing enclosing said control unit, said gyroscope, said laser diode and said color LED; and
    a fastening system attached to said casing, wherein said vibration motor is embedded into said fastening system.

2. The sensory electronic device of claim 1, wherein said electronic system further comprises a power source and a switch.

3. The sensory electronic device of claim 1, wherein said electronic system further comprises a wireless communication module.

4. The sensory electronic device of claim 2, wherein said casing further encloses said power source, said switch, and said gyroscope.

5. The sensory electronic device of claim 3, wherein said casing further encloses said wireless communication module.

6. The sensory electronic device of claim 1, wherein said casing includes a base and a top cover positioned on top of said base.

7. The sensory electronic device of claim 6, wherein said top cover includes an opening accommodating a power button.

8. The sensory electronic device of claim 1, wherein said base includes a lens receiving light emitted by said laser diode and projecting said light into a visible horizontal line.

9. The sensory electronic device of claim 6, wherein said power button is operatively connected to a switch of said electronic system.

10. The sensory electronic device of claim 1, wherein said fastening system includes:
    a first extendable element having a first coupling end configured to be attached to said casing; and a second extendable element having a second coupling end configured to be attached to said casing, wherein said vibration motor is embedded into another end of said second extendable element.

11. The sensory electronic device of claim 10, wherein said second extendable element further comprises an inner cavity longitudinally extending from an upper entrance opening provided on said second coupling end to a lower exit opening provided on said another end, said inner cavity encloses connection wires that are received at said upper entrance opening and exit at said lower exit opening so that the vibration motor is connected to said control unit.

12. The sensory electronic device of claim 10, wherein said second extendable element further comprises a covering element covering said vibration motor.

13. The sensory electronic device of claim 1, wherein said fastening system comprises an attaching element that is slidable into a rail system provided on said casing.

14. The sensory electronic device of claim 4, wherein said casing further comprises a charging port opening configure to receive an external charging cable.

15. The sensory electronic device of claim 3, wherein said electronic system is remotely controlled via said wireless communication module.

16. The sensory electronic device of claim 1, wherein said electronic system is controlled via said switch.

17. The sensory electronic device of claim 1, wherein said laser diode is activated when said control unit determines that said gyroscope has a predetermined inclination so that light emitted by said laser diode is projected as a visible horizontal line on the ground.

18. The sensory electronic device of claim 1, wherein said vibration motor is controlled by said control unit to vibrate at a selected speed, intensity, time and frequency.

19. The sensory electronic device of claim 1, wherein said laser diode and said color LED are remotely controlled by a smartphone.

20. A method for the rehabilitation of patients with Parkinson's disease using the sensory electronic device of claim 1, wherein said sensory electronic device is in contact with a patient's body so that said vibration motor is actuated to vibrate and said laser diode emits light that is projected as a visible horizontal line guide on the ground.

* * * * *